(12) United States Patent
Meng et al.

(10) Patent No.: US 8,809,590 B2
(45) Date of Patent: Aug. 19, 2014

(54) METHOD FOR INDUSTRIALLY PREPARING NITROGEN SUBSTITUTED AMINO-5,6,7,8-TETRAHYDRONAPHTHOL

(75) Inventors: Qingguo Meng, Shandong (CN); Mina Yang, Shandong (CN); Tao Wang, Shandong (CN); Qilin Wang, Shandong (CN); Jun Li, Beijing (CN); Zheng Ruan, Shandong (CN)

(73) Assignee: Shan Dong Luye Pharmaceutical Co., Ltd., Shandong (CN)

( * ) Notice: Subject to any disclaimer, the term of this patent is extended or adjusted under 35 U.S.C. 154(b) by 0 days.

(21) Appl. No.: 14/128,131

(22) PCT Filed: Jun. 21, 2012

(86) PCT No.: PCT/CN2012/000863
§ 371 (c)(1),
(2), (4) Date: Dec. 20, 2013

(87) PCT Pub. No.: WO2013/000273
PCT Pub. Date: Jan. 3, 2013

(65) Prior Publication Data
US 2014/0121380 A1    May 1, 2014

(30) Foreign Application Priority Data

Jun. 27, 2011  (CN) .......................... 2011 1 0179616

(51) Int. Cl.
| C07C 211/38 | (2006.01) |
| C07C 215/46 | (2006.01) |
| C07C 213/00 | (2006.01) |
| C07D 333/20 | (2006.01) |
| C07C 217/52 | (2006.01) |
| C07D 213/36 | (2006.01) |
| C07C 213/08 | (2006.01) |

(52) U.S. Cl.
CPC ............ *C07D 333/20* (2013.01); *C07C 215/46* (2013.01); *C07C 213/00* (2013.01); *C07C 2102/10* (2013.01); *C07C 217/52* (2013.01); *C07D 213/36* (2013.01); *C07C 213/08* (2013.01)

USPC ......................................................... 564/428

(58) Field of Classification Search
CPC ..................................................... C07C 211/38
See application file for complete search history.

(56) References Cited

U.S. PATENT DOCUMENTS

| 4,410,519 A | 10/1983 | Seiler et al. |
| 5,382,596 A | 1/1995 | Sleevi et al. |

FOREIGN PATENT DOCUMENTS

| WO | 01/38321 A1 | 5/2001 |
| WO | 2010-066755 A1 | 6/2010 |
| WO | 2011/026318 A1 | 3/2011 |

OTHER PUBLICATIONS

International Search Report issued in PCT/CN2012/000863 mailed on Sep. 27, 2012 (5 pages).

*Primary Examiner* — Andrew D Kosar
*Assistant Examiner* — John S Kenyon
(74) *Attorney, Agent, or Firm* — Osha Liang LLP

(57) ABSTRACT

A method for industrially preparing a nitrogen substituted 6-amino-5,6,7,8-tetrahydronaphthol includes reacting a nitrogen substituted amino-5,6,7,8-tetrahydronaphthol compound of formula (II) with a 2-substituted ethyl sulfonate compound of formula (III) under an alkaline condition and in the presence of a sulfite.

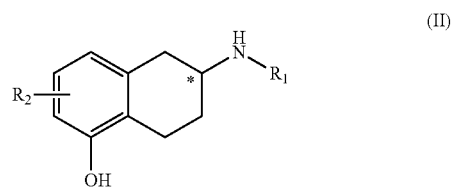

(II)

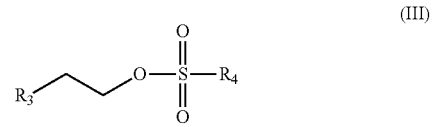

(III)

20 Claims, No Drawings

METHOD FOR INDUSTRIALLY PREPARING NITROGEN SUBSTITUTED AMINO-5,6,7,8-TETRAHYDRONAPHTHOL

CROSS-REFERENCE TO RELATED APPLICATIONS

This is a national stage application based on PCT/CN2012/000863, filed on Jun. 21, 2012, which claims priority to Chinese Patent Application No. 201110179616.6, filed on Jun. 27, 2011. This application claims the priority of these prior applications and incorporates their disclosures by reference in their entireties.

FIELD

The present disclosure relates to a method for industrially preparing a nitrogen substituted amino-5,6,7,8-tetrahydronaphthol.

BACKGROUND

Methods for preparing nitrogen substituted amino-5,6,7,8-tetrahydronaphthols have been disclosed in the following documents.

U.S. Pat. No. 4,410,519 (publication date: Oct. 18, 1983) discloses a reaction, by which the amino group of amino-5,6,7,8-tetrahydronaphthol is alkylated while forming acidic by-products (e.g., ZH). The reaction is represented below, in which $R_4$ is alkyl containing 1-4 carbon atoms. The alkylating agent is represented as $R_3$-A-Z, wherein A is —$(CH_2)n$-, n is an integer ranging from 1 to 5; and Z is a leaving group such as alkyl sulfonyloxy or aryl sulfonyloxy. A base may be optionally present.

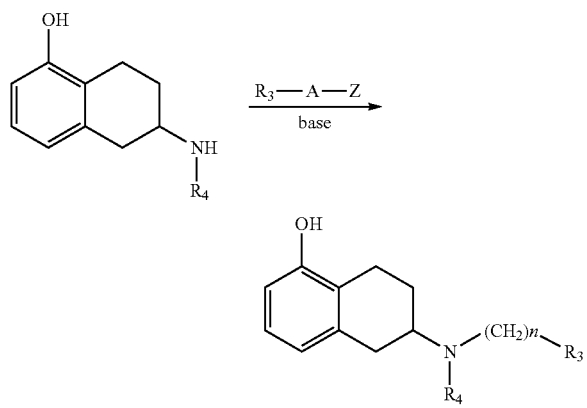

U.S. Pat. No. 5,382,596 (publication date: Jan. 17, 1995) discloses a reaction as followed in the presence of a base (i.e., a tertiary amine); wherein $R_4$ is a straight alkyl chain containing 1-3 carbon atoms or cyclopropyl methyl; $R_6$ is —$(CH_2)$n-$R_3$, n is an integer ranging from 1 to 4, and $R_3$ is alkoxy, cycloalkoxy or a cyclic ether.

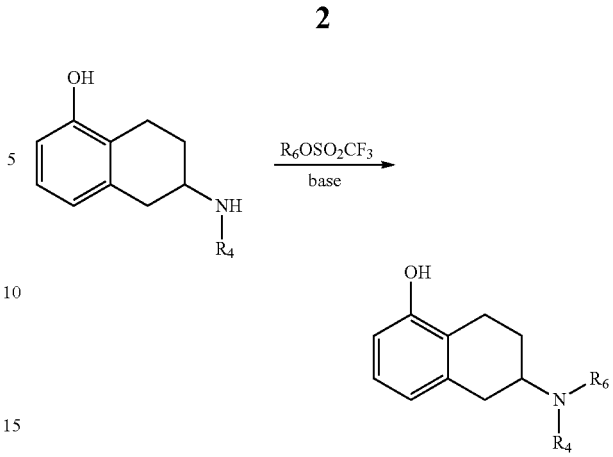

WO 01/38321 discloses the following reaction, in which a base used in the reaction is an alkali carbonate or a bicarbonate, the amount of which is less than 1.9 times by mole as compare to the starting material; $R_1$ is OA; $R_2$ is H or OA, in which A is H, a straight or branched alkyl containing 1-3 carbon atoms; $R_3$ is alkoxy, cycloalkoxy, optionally substituted phenyl, 3-pyridyl or 4-pyridyl; n is an integer ranging from 1 to 5; and Z is a leaving group.

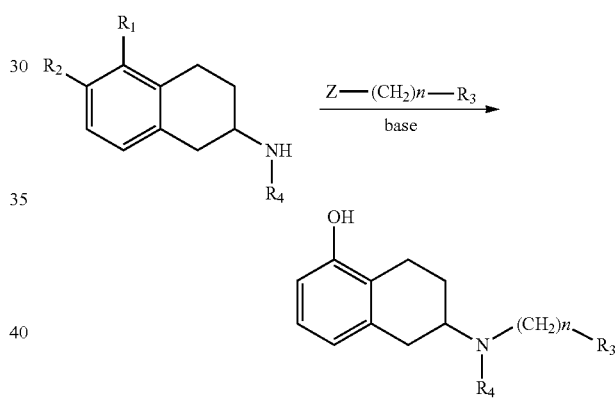

The bases used in the above reactions may only neutralize the acidic by-products generated in the alkylation reactions. However, because the reactions generally need to be carried out at a high temperature for a long time, the starting material containing the phenolic hydroxyl moiety may be easily oxidized to form a number of additional by-products. Therefore, the above reactions not only necessitate multiple purification process steps, but also decrease the reaction yield.

In WO 01/38321, by reducing the amount of the alkali carbonate, plenty of purification steps may be avoided, and the side reactions may be reduced. However, an increased amount of the alkylating agent may be needed to improve the yield of the target product, thus greatly increasing the production cost, and significantly reducing the yield in the large scale production, rendering it unsuitable for industrial productions.

SUMMARY

Provided herein includes a method for preparing a nitrogen substituted amino-5,6,7,8-tetrahydronaphthol with high yields, which may reduce the production cost and is therefore suitable for large scale industrial productions.

The above object of the present invention is carried out by the following technical solutions.

The present invention provides a method for preparing a compound of formula (I), comprising

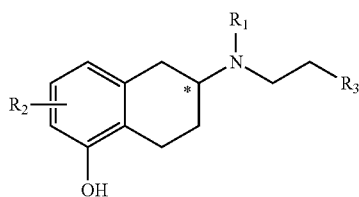

reacting a compound of formula (II) with a compound of formula (III) under an alkaline condition and in the presence of a sulfite,

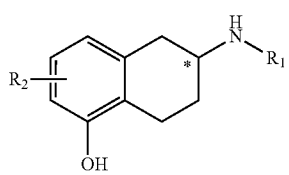

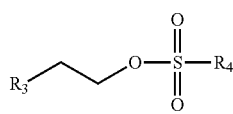

wherein, (*) represents a chiral center; the compound of formula (I) and the compound of formula (II) is a R or S configuration or a racemic mixture;

$R_1$ is a straight or branched alkyl containing 1-4 carbon atoms;

$R_2$ is hydrogen, a straight or branched alkyl containing 1-4 carbon atoms;

$R_3$ is a straight or branched alkyl containing 1-6 carbon atoms, alkoxy, cycloalkoxy, an optionally substituted phenyl, a heterocyclyl; and $R_4$ is alkyl, haloalkyl, optionally substituted aryl.

In one preferred embodiment of present invention, the chiral center (*) of the compound of formula (I) and formula (II) is S configuration, R3 is thienyl or pyridyl, R4 is methyl, trifluoromethyl, methylphenyl or nitrophenyl.

In another preferred embodiment of present invention, R1 is methyl, ethyl or n-propyl; R2 is methyl or hydrogen; R3 is 3-pyridyl or 2-thienyl; and R4 is 4-methylphenyl or 4-nitrophenyl.

In a further preferred embodiment of present invention, R1 is n-propyl, R2 is hydrogen, R3 is 2-thienyl, and R4 is 4-methylphenyl.

The sulfite is alkaline metal sulfites including sodium sulfite and potassium sulfite; alkaline earth metal sulfites including magnesium sulfite and calcium sulfite; or other sulfites including ammonium sulfite and zinc sulfite, preferably, sodium sulfite or potassium sulfite.

In one preferred embodiment of present invention, the molar ratio of the sulfite to the compound of formula (II) is (0.8-2.5):1, preferably 1.3:1.

In a further preferred embodiment of present invention, the molar ratio of the compound of formula (III) to the compound of formula (II) is (1.1-5.0):1, preferably 1.5:1.

In other embodiments, the method further comprising converting the compound of formula (I) to a salt form.

DETAILED DESCRIPTION

Disclosed herein includes a method for preparing a nitrogen substituted amino-5,6,7,8-tetrahydronaphthol of formula (I) is provided.

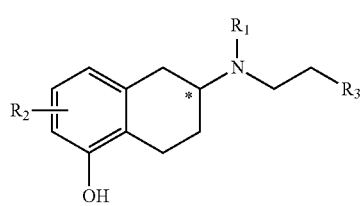

In particular, the method comprises reacting a compound of formula (II) with a compound of formula (III) under analkaline condition and in the presence of a sulfite to obtain the compound of formula (I),

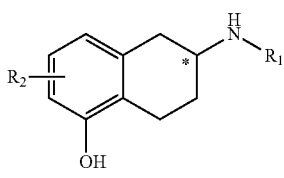

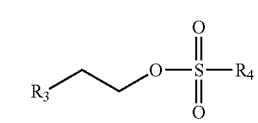

wherein, (*) represents a chiral center; the compound of formula (I) and the compound of formula (II) is in a R or S configuration or a racemic mixture; $R_1$ is straight or branched alkyl containing 1-4 carbon atoms; $R_2$ is hydrogen, a straight or branched alkyl containing 1-4 carbon atoms; $R_3$ is a straight or branched alkyl containing 1-6 carbon atoms, alkoxy, cycloalkoxy, an optionally substituted phenyl, or a heterocyclyl (e.g., thienyl or pyridyl); and $R_4$ is alkyl (e.g. methyl), haloalkyl (e.g., trifluoromethyl), optionally substituted aryl (e.g., methylphenyl or nitrophenyl).

As used herein, "straight or branched alkyl" or simply "alkyl" refers to a saturated aliphatic hydrocarbon radical. In various embodiments, the straight or branched alkyl may contain up to 4 carbons, or up to 6 carbons. Representative straight or branched alkyl of 1-6 carbon atoms include, for example, methyl, ethyl, n-propyl, n-butyl, n-pentyl, n-hexyl, isopropyl, sec-butyl, isobutyl, tert-butyl, isopentyl, and the like. Unless specified otherwise, the straight or branched alkyl may be optionally substituted, in which at least one hydrogen atom of the alky moiety is replaced with a substituent, as defined herein.

"Alkoxy" refers to the radical: —O-alkyl, such as methoxy, ethoxy, and the like.

"Aryl" refers to an aromatic monocyclic or multicyclic hydrocarbon ring system consisting only of hydrogen and carbon and containing from six to eighteen carbon atoms, where the ring system may be partially or fully saturated. Aryl groups include, but are not limited to, groups such as fluorenyl, phenyl and naphthyl. Unless otherwise specified, "aryl" can be optionally substituted with a substituent, as defined herein. Thus, "optionally substituted aryl" encompasses unsubstituted aryl (e.g., phenyl) and substituted aryl (e.g., methylphenyl, and nitrophenyl).

"Cycloalkoxy" refers to the radical: —O-cycloalkyl. Cycloalkyl refers to a nonaromatic cyclic hydrocarbon having 5-8 carbons. Examples of cycloalkoxy include cyclopentoxy, or cyclohexoxy.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Exemplary heterocyclyl include, without limitation, benzofuranyl, thienyl, benzothienyl, 1,3-benzodioxolyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Unless otherwise specified, "heterocyclyl" can be optionally substituted with a substituent, as defined herein. Thus, "optionally substituted heterocyclyl" encompasses unsubstituted heterocyclyl and substituted heterocyclyl.

A "substituent" includes oxo, halogen, hydroxy, cyano, nitro, amino, alkylamino, dialkylamino, alkyl, alkoxy, haloalkyl, substituted alkyl, aryl, substituted aryl, heterocyclyl, substituted heterocyclyl, —NR$_a$R$_b$, —NR$_a$C(=O)R$_b$, —NR$_a$C(=O)NR$_a$R$_b$, —NR$_a$C(=O)OR$_b$, —NR$_a$S(=O)$_2$R$_b$, —OR$_a$, —C(=O)R$_a$ —C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O) NR$_a$R$_b$, —OS(=O)$_2$R$_a$ and —S(=O)$_2$OR$_a$, wherein R$_a$ and R$_b$ are the same or different and independently hydrogen, alkyl, haloalkyl, substituted alkyl, alkoxy, aryl, or substituted aryl.

In various embodiments, the chiral center is in a pure R or S configuration.

In preferred embodiments, the chiral center (*) is S configuration; R$_1$ is methyl, ethyl or n-propyl; R$_2$ is methyl or a hydrogen; R$_3$ is 3-pyridyl or 2-thienyl; and R$_4$ is 4-methylphenyl or 4-nitrophenyl. More preferably, R$_1$ is n-propyl, R$_2$ is hydrogen, R$_3$ is 2-thienyl, and R$_4$ is 4-methylphenyl. That is, the compound of formula (I) is (S)-5,6,7,8-tetrahydro-6-[propyl[2-(2-thienyl)ethyl]amino]-1-naphthol; the compound of formula (II) is (S)-5,6,7,8-tetrahydro-6-propylamino-1-naphthol; and the compound of formula (III) is 2-(2-thienyl)ethyl 4-methylbenzenesulfonate.

The reaction route is shown as follows:

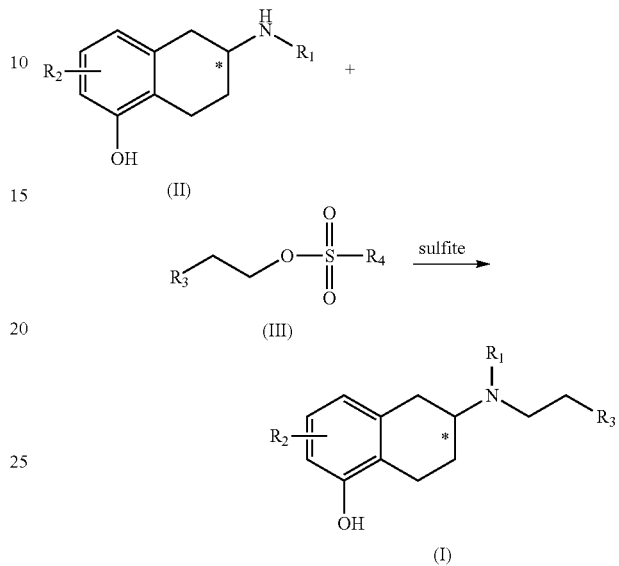

The molar ratio of the compound of formula (III) to the compound of formula (II) is typically (1.1-5.0):1, preferably 1.5:1. These starting materials may be prepared by methods known in the art. See e.g., WO 01/38321.

The molar ratio of the sulfite to the compound of formula (II) is typically (0.8-2.5):1, preferably 1.3:1. The sulfite is selected from alkaline metal sulfites including sodium sulfite and potassium sulfite; alkaline earth metal sulfites including magnesium sulfite and calcium sulfite; or other sulfites including ammonium sulfite and zinc sulfite; preferably sodium sulfite or potassium sulfite.

Advantageously, the sulfite neutralizes the acidic by-products generated by the alkylating agent, i.e., the compound of formula (III) in the reaction, thereby preventing the acidic by-products from further degrading the compound of formula (III). Moreover, the sulfite is believed to act as an antioxidant, thereby effectively preventing the compound of formula (II), which contains the labile phenolic hydroxyl moiety, from being oxidized to form by-products under reaction conditions of high temperature and long time. As a result, various by-products and steps of separation and purification may be avoided, and production efficiency is improved. Meanwhile, the reaction is carried out more completely without having to significantly increase of the amount of the alkylating agent, thus improving the reaction yield.

The method for preparing the nitrogen substituted amino-5,6,7,8-tetrahydronaphthol of formula (I) according to an embodiment of the present disclosure may ensure high yield of a target product in large scale industrial productions and reduce the industrial production cost by reducing the amount of the alkylating agent.

A reaction solvent in the method is xylene, and a reaction temperature is generally 140° C. to 145° C.

In further embodiments, the methods describe herein further comprise converting the compound of formula (I) into a salt form. More specifically, the tertiary amino group of a compound of formula (I) can be converted into a quaternary ammonium salt in the presence of an acid (HX). One example of a suitable acid is hydrogen chloride, providing a hydrochlorate salt of formula (I), shown below (X is Cl⁻):

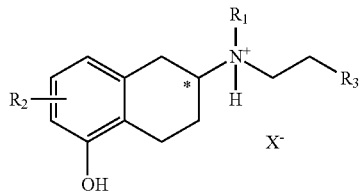

In further embodiments, the compound of formula (I) is rotigotine.

EXAMPLES

The present disclosure will be further illustrated by the following examples and test examples, which will not limit the scope of the present invention in any way.

Example 1

2.00 kg (9.74 mol) of (S)-5,6,7,8-tetrahydro-6-propylamino-1-naphthol, 4.12 kg (14.62 mol) of 2-(2-thienyl)ethyl 4-methylbenzenesulfonate (with a sulfonate/starting material mole ratio of 1.5/1), 0.61 kg (4.875 mol) of sodium sulfite (with a sodium sulfite/starting material mole ratio of 0.5/1) and 25 L of xylene were mixed to form a mixture, and the mixture was refluxed. After 48 hours, the reaction was not carried out completely. The reaction was continued for 96 hours. The mixture was cooled to room temperature, and washed with an appropriate amount of water. Active carbon was added to decolorize the mixture. The mixture was filtered and left standing. An organic phase was reserved and concentrated under vacuum to obtain 0.40 kg of a product (S)-5,6,7,8-tetrahydro-6-[propyl[2-(2-thienyl)ethyl]amino]-1-naphthol, which was converted into a hydrochlorate thereof. The yield was 11.7%.

Example 2

2.00 kg (9.74 mol) of (S)-5,6,7,8-tetrahydro-6-propylamino-1-naphthol, 4.12 kg (14.62 mol) of 2-(2-thienyl)ethyl 4-methylbenzenesulfonate (with a sulfonate/starting material mole ratio of 1.5/1), 0.98 kg (7.80 mol) of sodium sulfite (with a sodium sulfite/starting material mole ratio of 0.8/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.41 kg of a product (S)-5,6,7,8-tetrahydro-6-[propyl[2-(2-thienyl)ethyl]amino]-1-naphthol, which was converted into a hydrochlorate thereof. The yield was 70.3%.

Example 3

2.00 kg (11.28 mol) of (S)-5,6,7,8-tetrahydro-6-methylamino-1-naphthol, 4.78 kg (16.94 mol) of 2-(2-thienyl)ethyl 4-methylbenzenesulfonate (with a sulfonate/starting material mole ratio of 1.5/1), 1.85 kg (14.68 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 3.06 kg of a product (S)-5,6,7,8-tetrahydro-6-[methyl[2-(2-thienyl)ethyl]amino]-1-naphthol, which was converted into a hydrochlorate thereof. The yield was 83.7%.

Example 4

2.00 kg (10.46 mol) of (S)-5,6,7,8-tetrahydro-6-ethylamino-1-naphthol, 4.91 kg (15.70 mol) of 2-(2-thienyl)ethyl 4-nitrobenzenesulfonate (with a sulfonate/starting material mole ratio of 1.5/1), 2.15 kg (13.60 mol) of potassium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.92 kg of a product (S)-5,6,7,8-tetrahydro-6-[ethyl[2-(2-thienyl)ethyl]amino]-1-naphthol, which was converted into a hydrochlorate thereof. The yield was 82.6%.

Example 5

2.00 kg (9.12 mol) of (S)-5,6,7,8-tetrahydro-4-methyl-6-propylamino-1-naphthol, 3.86 kg (13.70 mol) of 2-(2-thienyl)ethyl 4-methylbenzenesulfonate (with a sulfonate/starting material mole ratio of 1.5/1), 1.38 kg (11.87 mol) of ammonium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.60 kg of a product (S)-5,6,7,8-tetrahydro-4-methyl-6-[propyl[2-(2-thienyl)ethyl]amino]-1-naphthol, which was converted into a hydrochlorate thereof. The yield was 77.9%.

Example 6

2.00 kg (9.74 mol) of (S)-5,6,7,8-tetrahydro-6-propylamino-1-naphthol, 4.12 kg (14.62 mol) of 2-(2-thienyl)ethyl 4-methylbenzenesulfonate (with a sulfonate/starting material mole ratio of 1.5/1), 3.07 kg (24.38 mol) of sodium sulfite (with a sodium sulfite/starting material mole ratio of 2.5/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.47 kg of a product (S)-5,6,7,8-tetrahydro-6-[propyl[2-(2-thienyl)ethyl]amino]-1-naphthol, which was converted into a hydrochlorate thereof. The yield was 72.0%.

Example 7

2.00 kg (9.74 mol) of (S)-5,6,7,8-tetrahydro-6-propylamino-1-naphthol, 4.12 kg (14.62 mol) of 2-(2-thienyl)ethyl 4-methylbenzenesulfonate (with a sulfonate/starting material mole ratio of 1.5/1), 3.69 kg (29.25 mol) of sodium sulfite (with a sodium sulfite/starting material mole ratio of 3.0/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain a residue. The residue was separated by silica gel column chromatography, and eluted with ethyl acetate and hexane (1:19), to obtain 1.64 kg of (S)-5,6,7,8-tetrahydro-6-[propyl[2-(2-thienyl)ethyl]amino]-1-naphthol, which was converted into a hydrochlorate thereof. The yield was 47.8%.

Example 8

2.00 kg (9.74 mol) of (S)-5,6,7,8-tetrahydro-6-propylamino-1-naphthol, 4.12 kg (14.62 mol) of 2-(2-thienyl)ethyl 4-methylbenzenesulfonate (with an auxiliary material/starting material mole ratio of 1.5/1), 12.28 kg (97.49 mol) of sodium sulfite (with a sodium sulfite/starting material mole ratio of 10.0/1) and 25 L of xylene were mixed to form a mixture, and the mixture was refluxed. After 48 hours, the reaction was not carried out completely. The reaction was continued carrying out for 72 hours. After analyzed, it was indicated that there were a plenty of by-products in the product mixture. Due to low yield, the separation of the desired product (S)-5,6,7,8-tetrahydro-6-[propyl[2-(2-thienyl)ethyl]amino]-1-naphthol was abandoned.

Example 9

2.00 kg (9.74 mol) of (S)-5,6,7,8-tetrahydro-6-propylamino-1-naphthol, 2.20 kg (7.80 mol) of 2-(2-thienyl)ethyl 4-methylbenzenesulfonate (with a sulfonate/starting material mole ratio of 0.8/1), 1.60 kg (12.67 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 1.51 kg of a product (S)-5,6,7,8-tetrahydro-6-[propyl[2-(2-thienyl)ethyl]amino]-1-naphthol, which was converted into a hydrochlorate thereof. The yield was 44.0%.

Example 10

2.00 kg (9.74 mol) of (S)-5,6,7,8-tetrahydro-6-propylamino-1-naphthol, 3.02 kg (10.72 mol) of 2-(2-thienyl)ethyl 4-methylbenzenesulfonate (with a sulfonate/starting material mole ratio of 1.1/1), 1.60 kg (12.67 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.40 kg of a product (S)-5,6,7,8-tetrahydro-6-[propyl[2-(2-thienyl)ethyl]amino]-1-naphthol, which was converted into a hydrochlorate thereof. The yield was 70.0%.

Example 11

2.00 kg (9.74 mol) of (S)-5,6,7,8-tetrahydro-6-propylamino-1-naphthol, 3.57 kg (12.67 mol) of 2-(2-thienyl)ethyl 4-methylbenzenesulfonate (with a sulfonate/starting material mole ratio of 1.3/1), 1.60 kg (12.67 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.60 kg of a product (S)-5,6,7,8-tetrahydro-6-[propyl[2-(2-thienyl)ethyl]amino]-1-naphthol, which was converted into a hydrochlorate thereof. The yield was 75.8%.

Example 12

2.00 kg (9.74 mol) of (S)-5,6,7,8-tetrahydro-6-propylamino-1-naphthol, 4.12 kg (14.62 mol) of 2-(2-thienyl)ethyl 4-methylbenzenesulfonate (with a sulfonate/starting material mole ratio of 1.5/1), 1.60 kg (12.67 mol) of sodium sulfite (with a sodium sulfite/starting material mole ratio of 1.3/1,) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.80 kg of a product (S)-5,6,7,8-tetrahydro-6-[propyl[2-(2-thienyl)ethyl]amino]-1-naphthol, which was converted into a hydrochlorate thereof. The yield was 81.7%.

Example 13

2.00 kg (9.74 mol) of (S)-5,6,7,8-tetrahydro-6-propylamino-1-naphthol, 13.75 kg (48.75 mol) of 2-(2-thienyl)ethyl 4-methylbenzenesulfonate (with a sulfonate/starting material mole ratio of 5.0/1), 1.60 kg (12.67 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.46 kg of a product (S)-5,6,7, 8-tetrahydro-6-[propyl[2-(2-thienyl)ethyl]amino]-1-naphthol, which was converted into a hydrochlorate thereof. The yield was 71.8%.

Example 14

2.00 kg (9.74 mol) of (±)-5,6,7,8-tetrahydro-6-propylamino-1-naphthol, 4.12 kg (14.62 mol) of 2-(2-thienyl)ethyl 4-methylbenzenesulfonate (with a sulfonate/starting material mole ratio of 1.5/1), 1.60 kg (12.67 mol) of sodium sulfite (with a sodium sulfite/starting material mole ratio of 1.3/1) and 25 L of xylene were mixed to form a mixture, and the mixture was refluxed. After 60 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.70 kg of a product (±)-5,6,7,8-tetrahydro-6-[propyl[2-(2-thienyl)ethyl]amino]-1-naphthol, which was converted into a hydrochlorate thereof. The yield was 78.8%.

Example 15

2.00 kg (9.12 mol) of (S)-5,6,7,8-tetrahydro-4-methyl-6-propylamino-1-naphthol, 1.89 kg (13.70 mol) of n-propyl methanesulphonate (with a sulfonate/starting material mole ratio of 1.5/1), 1.49 kg (11.87 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.05 kg of a product (S)-5,6,7,8-tetrahydro-4-methyl-6-(dipropylamino)-1-naphthol, which was converted into a hydrochlorate thereof. The yield was 75.5%.

Example 16

2.00 kg (9.12 mol) of (S)-5,6,7,8-tetrahydro-4-methyl-6-propylamino-1-naphthol, 2.85 kg (13.70 mol) of n-octyl methanesulphonate (with a sulfonate/starting material mole ratio of 1.5/1), 1.49 kg (11.87 mol) of sodium sulfite (with a sodium sulfite/starting material mole ratio of 1.3/1) and 25 L of xylene were mixed to form a mixture, and the mixture was refluxed. After 60 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.37 kg of a product (S)-5,6,7,8-tetrahydro-4-methyl-6-(N-octyl-N-propylamino)-1-naphthol, which was converted into a hydrochlorate thereof. The yield was 70.6%.

Example 17

2.00 kg (9.12 mol) of (S)-5,6,7,8-tetrahydro-4-methyl-6-propylamino-1-naphthol, 2.11 kg (13.70 mol) of 2-methoxylethyl methanesulphonate (with a sulfonate/starting material mole ratio of 1.5/1), 1.49 kg (11.87 mol) of sodium sulfite (with a sodium sulfite/starting material mole ratio of 1.3/1) and 25 L of xylene were mixed to form a mixture, and the mixture was refluxed. After 60 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.05 kg of a product (S)-5,6,7,8-tetrahydro-4-methyl-6-[N-(2-methoxyethyl)-N-propylamino]-1-naphthol, which was converted into a hydrochlorate thereof. The yield was 71.6%.

Example 18

2.00 kg (8.085 mol) of (S)-5,6,7,8-tetrahydro-4-propyl-6-propylamino-1-naphthol, 3.35 kg (12.14 mol) of 2-(cyclohexyloxy)ethyl trifluoromethanesulfonate (with a sulfonate/starting material mole ratio of 1.5/1), 1.33 kg (10.52 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.48 kg of a product (S)-5,6,7,8-tetrahydro-4-propyl-6-[N-[2-(cyclohexyloxy)ethyl]-N-propylamino]-1-naphthol, which was converted into a hydrochlorate thereof. The yield was 74.8%.

Example 19

2.00 kg (8.085 mol) of (S)-5,6,7,8-tetrahydro-4-propyl-6-propylamino-1-naphthol, 3.25 kg (12.14 mol) of 2-(4-methylphenyl)ethyl trifluoromethanesulfonate (with a sulfonate/starting material mole ratio of 1.5/1), 1.33 kg (10.52 mol) of sodium sulfite (with a sodium sulfite/starting material mole ratio of 1.3/1) and 25 L of xylene were mixed to form a mixture, and the mixture was refluxed. After 48 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.52 kg of a product (S)-5,6,7,8-tetrahydro-4-propyl-6-[N-[2-(4-methylphenyl)ethyl]-N-propylamino]-1-naphthol, which was converted into a hydrochlorate thereof. The yield was 77.5%.

Example 20

2.00 kg (8.085 mol) of (S)-5,6,7,8-tetrahydro-4-propyl-6-propylamino-1-naphthol, 3.10 kg (12.14 mol) of 2-(3-pyridyl)ethyl trifluoromethanesulfonate (with a sulfonate/starting material mole ratio of 1.5/1), 1.33 kg (10.52 mol) of sodium sulfite (with a sodium sulfite/starting material mole ratio of 1.3/1) and 25 L of xylene were mixed to form a mixture, and the mixture was refluxed. After 60 hours, the reaction was stopped. The mixture was cooled to room temperature, and washed with an appropriate amount of water. Active carbon was added to decolorize the mixture. The mixture was filtered and left standing. An organic phase was reserved and concentrated under vacuum to obtain 2.41 kg of a product (S)-5,6,7,8-tetrahydro-4-propyl-6-[N-[2-(3-pyridyl)ethyl]-N-propylamino]-1-naphthol, which was converted into a hydrochlorate thereof. The yield was 76.6%.

Test Example 1

Results of the Present Disclosure as Compared with WO 01/38321

The respective synthetic approaches of the present disclosure and WO 01/38321 were used for preparing nitrogen substituted amino-5,6,7,8-tetrahydronaphthols respectively. The amount of raw materials, the amount of sodium carbonate/sodium sulfite, the reaction scales and the final yield were compared.

Data source: experimental data of Examples 1-4 in WO 01/38321 experimental data of Examples 10-13 in the present disclosure

It may be seen from the results shown in Table 1 that in the preparation method disclosed in WO 01/38321, the amount of the alkylating agent (sulphonate) needed be increased to improve the yield. For example, on a laboratory scale, only when the sulphonate to the 6-amino-5,6,7,8-tetrahydronaphthol molar ratio is 5, the yield may reach 80% or higher; while in large scale productions, the yield will be reduced significantly and only may reach 59%. In contrast, in the preparation method provided in the present disclosure, when the sulphonate to the 6-amino-5,6,7,8-tetrahydronaphthol molar ratio is 1.1, in large scale production, the yield may reach 70% or higher. Therefore, in accordance with the preparation method provided in the present disclosure, a relatively small amount of the alkylating agent sulphonate is used to obtain the final product with high yields, thus making the reaction suitable for large scale industrial productions at a reasonable production cost.

TABLE 1

Comparison between Test Results of the Present Disclosure and CN1391569

| Test Solution | Example | Base Molar Ratio* | Reaction Scale/ Starting Material (g) | Sulphonate Mole Ratio Δ | Yield |
|---|---|---|---|---|---|
| WO 01/38321 | Example 1 | 0.6 | 0.7 | 5 | 84% |
| | Example 2 | 0.6 | 13100 | 2.8 | 59% |
| | Example 3 | 9.4 | 0.6 | 1.3 | Abandoned due to low yield |
| | Example 4 | 3.1 | 388 | 1.1 | 55% |
| The Present Disclosure | Example 10 | 1.3 | 2000 | 1.1 | 70.0% |
| | Example 11 | 1.3 | 2000 | 1.3 | 75.8% |
| | Example 12 | 1.3 | 2000 | 1.5 | 81.7% |
| | Example 13 | 1.3 | 2000 | 5.0 | 71.8% |

*The base molar ratio refers to the ratio of sodium carbonate/sodium sulfite to the starting material 6-amino-5,6,7,8-tetrahydronaphthol for WO 01/38321; and the ratio of sodium sulfite to the 6-amino-5,6,7,8-tetrahydronaphthol for the present disclosure.
Δ The ratio of 2-(2-thienyl)ethyl 4-methylbenzenesulfonate to 6-amino-5,6,7,8-tetrahydronaphthol Test Example 2

Selection Test of the Amount of Sodium Sulfite

At a given ratio of 2-(2-thienyl)ethyl 4-methylbenzenesulfonate to 6-amino-5,6,7,8-tetrahydronaphthol, the yields of the reaction products may depend on the amount of the sulfite.

Data source: experimental data of Examples 1-2, 6-8, 12 in the present disclosure It may be seen from the results shown in Table 2 that when the mole ratio of sodium sulfite to the starting material 6-amino-5,6,7,8-tetrahydronaphthol is 0.8-2.5, the yield of the final product may reach about 70%.

TABLE 2

Comparison between Results of Sodium Sulfite Molar Ratio in the Present Disclosure

| Example | Sulphonate Molar RatioΔ | Sodium Sulfite Molar Ratio* | Yield |
|---|---|---|---|
| Example 1 | 1.5 | 0.5 | 11.7% |
| Example 2 | 1.5 | 0.8 | 70.3% |
| Example 12 | 1.5 | 1.3 | 81.7% |
| Example 6 | 1.5 | 2.5 | 72.0% |
| Example 7 | 1.5 | 3.0 | 47.8% |
| Example 8 | 1.5 | 10.0 | Low yield |

*The sodium sulfite molar ratio refer to the ratio of sodium sulfite to the starting material 6-amino-5,6,7,8-tetrahydronaphthol.
ΔThe ratio of 2-(2-thienyl)ethyl 4-methylbenzenesulfonate to 6-amino-5,6,7,8-tetrahydronaphthol Test Example 3

Amount of Alkylating Agent Sulphonate

At a given amount of sodium sulfite, the yields of the reaction products may depend on the ratio of 2-(2-thienyl)ethyl 4-methylbenzenesulfonate to 6-amino-5,6,7,8-tetrahydronaphthol, i.e., the relative amount of the alkylating agent sulfonate.

Data source: experimental data of Examples 9-13 in the present disclosure

It may be seen from the results shown in Table 3 that when the mole ratio of 2-(2-thienyl)ethyl 4-methylbenzenesulfonate to 6-amino-5,6,7,8-tetrahydronaphthol is (1.1-5.0):1, the yield of the final product may reach more than 70%.

TABLE 3

Comparison between Results of Mole Ratios of Raw Materials in the Present Disclosure

| Example | Sodium Sulfite Mole Ratio* | Sulphonate Mole Ratio Δ | Yield |
|---|---|---|---|
| Example 9 | 1.3 | 0.8 | 44.0% |
| Example 10 | 1.3 | 1.1 | 70.0% |
| Example 11 | 1.3 | 1.3 | 75.8% |
| Example 12 | 1.3 | 1.5 | 81.7% |
| Example 13 | 1.3 | 5.0 | 71.8% |

*The sodium sulfite molar ratio refer to the ratio of sodium sulfite to the starting material 6-amino-5,6,7,8-tetrahydronaphthol
Δ The ratio of 2-(2-thienyl)ethyl 4-methylbenzenesulfonate to 6-amino-5,6,7,8-tetrahydronaphthol

What is claimed is:

1. A method for preparing a compound of formula (I), comprising:

(I)

$R_2$—[tetrahydronaphthalene with OH]—$N(R_1)$—CH$_2$CH$_2$—$R_3$ reacting a compound of formula (II) with a compound of formula (III) under an alkaline condition and in the presence of a sulfite, (II)

$R_2$—[tetrahydronaphthalene with OH]—NH—$R_1$ (III)

$R_3$—CH$_2$CH$_2$—O—S(=O)$_2$—$R_4$ wherein,
(*) represents a chiral center; the compound of formula (I) and the compound of formula (II) is an R or S configuration or a racemic mixture;

R₁ is a straight or branched alkyl containing 1-4 carbon atoms;

R₂ is hydrogen, a straight or branched alkyl containing 1-4 carbon atoms;

R₃ is a straight or branched alkyl containing 1-6 carbon atoms, alkoxy, cycloalkoxy, an phenyl or substituted phenyl or a heterocyclyl; and R₄ is alkyl, haloalkyl, aryl or substituted aryl wherein the sulfite is an alkaline metal sulfite, an alkaline earth metal sulfite, ammonium sulfite, or zinc sulfite wherein the substituted phenyl or the substituted aryl is substituted with a substituent selected from the group consisting of oxo, halogen, hydroxy, cyano, nitro, amino, alkylamino, dialkylamino, alkyl, alkoxy, haloalkyl, unsubstituted aryl, heterocyclyl, —NR$_a$R$_b$, —NR$_a$C(=O)R$_b$, —NR$_a$C(=O)NR$_a$R$_b$, —NR$_a$C(=O)OR$_b$, —NR$_a$S(=O)$_2$R$_b$, —OR$_a$, —C(=O)R$_a$—C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O)NR$_a$R$_b$, —OS(=O)$_2$R$_a$ and —S(=O)$_2$OR$_a$, wherein R$_a$ and R$_b$ are independently hydrogen, alkyl, haloalkyl, alkoxy, or unsubstituted aryl.

2. The method according to claim 1, wherein the chiral center (*) of the compound of formula (I) and formula (II) is S configuration.

3. The method according to claim 1, wherein R₃ is thienyl or pyridyl.

4. The method according to claim 1, wherein R₄ is methyl, trifluoromethyl, methylphenyl or nitrophenyl.

5. The method according to claim 1, wherein R₁ is methyl, ethyl or n-propyl; R₂ is methyl or hydrogen; R₃ is 3-pyridyl or 2-thienyl; and R₄ is 4-methylphenyl or 4-nitrophenyl.

6. The method according to claim 5, wherein R₁ is n-propyl, R₂ is hydrogen, R₃ is 2-thienyl, and R₄ is 4-methylphenyl.

7. The method according to claim 1, wherein the alkaline metal sulfite is sodium sulfite or potassium sulfite and the alkaline earth metal sulfite is magnesium sulfite or calcium sulfite.

8. The method according to claim 7 wherein the alkaline metal sulfite is sodium sulfite or potassium sulfite.

9. The method according to claim 1, wherein the molar ratio of the sulfite to the compound of formula (II) is (0.8-2.5):1.

10. The method according to claim 9, wherein the molar ratio of the sulfite to the compound of formula (II) is 1.3:1.

11. The method according to claim 1, wherein the molar ratio of the compound of formula (III) to the compound of formula (II) is (1.1-5.0):1.

12. The method according to claim 11, wherein the molar ratio of the compound of formula (III) to the compound of formula (II) is 1.5:1.

13. The method according to claim 1, wherein the compound of formula (I) is rotigotine.

14. The method according to claim 1, further comprising converting the compound of formula (I) to a salt form.

15. The method according to claim 14, wherein the salt form is hydrochlorate salt.

16. The method according to claim 2, wherein R₃ is thienyl or pyridyl.

17. The method according to claim 2, wherein R₄ is methyl, trifluoromethyl, methylphenyl or nitrophenyl.

18. The method according to claim 3, wherein R₄ is methyl, trifluoromethyl, methylphenyl or nitrophenyl.

19. The method according to claim 2, wherein R₁ is methyl, ethyl or n-propyl; R₂ is methyl or hydrogen; R₃ is 3-pyridyl or 2-thienyl; and R₄ is 4-methylphenyl or 4-nitrophenyl.

20. The method according to claim 3, wherein R₁ is methyl, ethyl or n-propyl; R₂ is methyl or hydrogen; R₃ is 3-pyridyl or 2-thienyl; and R₄ is 4-methylphenyl or 4-nitrophenyl.

* * * * *